United States Patent [19]

Aga et al.

[11] Patent Number: 5,656,308

[45] Date of Patent: *Aug. 12, 1997

[54] NON-REDUCING OLIGOSACCHARIDE WITH NEOTREHALOSE STRUCTURE, AND ITS PRODUCTION AND USES

[75] Inventors: Hajime Aga; Takashi Shibuya; Toshiyuki Sugimoto; Toshio Miyake, all of Okayama, Japan

[73] Assignee: Kabushiki Kaisha Hayashibara Seibutsu Kagaku Kenkyujo, Okayama, Japan

[*] Notice: The term of this patent shall not extend beyond the expiration date of Pat. No. 5,523,099.

[21] Appl. No.: 466,440

[22] Filed: Jun. 6, 1995

Related U.S. Application Data

[62] Division of Ser. No. 355,243, Dec. 9, 1994, Pat. No. 5,523,099.

[30] Foreign Application Priority Data

Dec. 15, 1993 [JP] Japan ................... 5-342187

[51] Int. Cl.$^6$ ............... A23L 1/00; A23L 1/09; A61K 7/42; C07H 3/06
[52] U.S. Cl. ............... 426/3; 426/48; 426/548; 426/658; 426/804; 424/59; 424/493; 514/54; 536/118; 536/123.1; 435/97; 435/99; 435/101; 435/193; 435/200; 435/195
[58] Field of Search ................... 426/3, 48, 548, 426/804; 420/658; 424/59, 493; 514/54; 536/118, 123.1; 435/97, 99, 101, 193, 200, 195

[56] References Cited

U.S. PATENT DOCUMENTS 5,298,616 3/1994 Hosang et al.
5,523,099 6/1996 Aga et al. ................... 426/3

FOREIGN PATENT DOCUMENTS

| 58-72598 | 4/1983 | Japan. |
| 58-23799 | 12/1983 | Japan. |
| 4179490 | 6/1992 | Japan. |
| 5252973 | 5/1993 | Japan. |
| 923265 | 3/1992 | WIPO. |

OTHER PUBLICATIONS

Fischer et al., "Oligosaccharide aus *Streptococcus lactis*," *Hoppe–Seyler's Z. Physiol. Chem.*, vol. 350, 1137–1147, (1969).

Ajisaka et al., "Regioselective syntheses of trehalose-containing trisaccharides using various glycohydrolases," *Carbohydrate Research*, 199:227–234 (1990).

Primary Examiner—Herbert J. Lilling
Attorney, Agent, or Firm—Browdy and Neimark

[57] ABSTRACT

Disclosed is a novel non-reducing oligosaccharide with neotrehalose structure represented by the general formula as shown by:

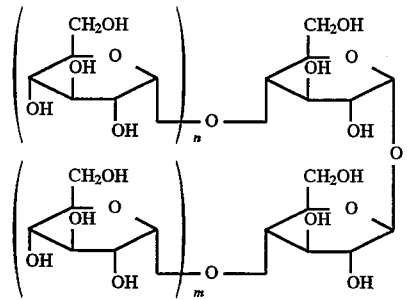

The oligosaccharide is obtainable by exposing an aqueous solution containing neotrehalose to a saccharide-transferring enzyme, and has a superior stability, reduced sweetness, appropriate viscosity, no susceptibility to crystallization and less fermentability. These features make it very useful in various compositions including foods, beverages, cosmetics and pharmaceuticals.

6 Claims, No Drawings

NON-REDUCING OLIGOSACCHARIDE WITH NEOTREHALOSE STRUCTURE, AND ITS PRODUCTION AND USES

This is a division of parent application Ser. No. 08/355, 243 filed Dec. 9, 1994, now U.S. Pat. No. 5,523,099.

BACKGROUND OF THE INVENTION

1. Field of the Invention

The present invention relates to a novel saccharide, a process to produce the same and also its uses, more particularly, to a non-reducing oligosaccharide as represented by the formula β-D-oligoglucosyl α-D-glucoside, α-D-oligoglucosyl β-D-glucoside or β-D-oligoglucosyl α-D-oligoglucoside and a process to produce the same, as well as to its uses.

2. Description of the Prior Art

There have been known several types of non-reducing oligosaccharides: a type where as found in sucrose, erlose, raffinose, melezitose and kestose, Glucose and fructose are bound via the α-1 and β-2 linkages, in other words, oligosaccharides having a sucrose structure in the molecules; sugar alcohols such as maltitol, maltotriitol and lactitol; and neotrehalose where glucose is bound each other via the α-1 and β-1 linkages. Oligosaccharides having a sucrose structure in the molecules are, however, less stable et the α-1 and β-2 linkages and readily decomposable in an acidic solution. Such less stability provides several restrictions in the processing of foods and the like. Sugar alcohols, which are usually prepared by hydrogenation at an elevated pressure, are excellent in stability, however, less digestible and assimilable in human body so that they have the drawback that when excessively taken they may induce diarrhea. While neotrehalose (α, β-trehalose) is stable and handles readily, and has a gentle and mild sweetness. As disclosed in Japan Patent Kokai No.176,490/92 or No.252,973/93 by this applicant, neotrehalose is orally or parenterally administered to human bodies and well metabolized and advantageously utilized as an energy source without toxicity and side effects. Furthermore, since neotrehalose is not readily fermentable by dental-carries-inducing microorganisms, it can be utilized as a less cariogenic sweetener. These superb properties are found in neotrehalose, however, for the sake of viscosity-imparting ability and moisture-retaining ability, the development of a higher molecular oligosaccharide exhibiting the properties of neotrehalose is expected.

SUMMARY OF THE INVENTION

The present invention is to provide a novel non-reducing oligosaccharide with neotrehalose structure in the molecule and a process to produce the same, as well as to provide uses thereof.

To establish such oligosaccharide and process, the present inventors have energetically investigated means which might bind saccharide moieties to either or both of the glucosyl groups in neotrehalose. The investigation led to the finding that the above objectives were attainable by allowing a saccharide-transferring enzyme to an aqueous solution which contained neotrehalose and an α-glucosyl saccharide, thus the present inventors accomplished the present invention. More particularly, the present invention does establish a novel non-reducing oligosaccharide where one or more additional glucosyl groups are bound to either or both of the glucosyl groups in neotrehalose, as well as establishing a process to produce the same and uses thereof where characteristics of the oligosaccharide such as superior stability, tastelessness or reduced sweetness and/or assimilability into calorie on oral intake are advantageously utilized.

DETAILED DESCRIPTION OF THE INVENTION

Although the non-reducing oligosaccharide of the present invention can be synthesized in chemical manner, with industrial viewpoint, it is much more favorable to employ biochemical reactions where aqueous solutions containing neotrehalose and α-glucosyl saccharides are exposed to saccharide-transferring enzymes. Neotrehaloses which are suitable in such a biochemical reaction are in syrup or powder with the highest possible neotrehalose content, Generally, 10 w/w % or higher, on a dry solid basis (d.s.b.), desirably, in syrup or crystalline powder with a neotrehalose content of 50 w/w % or higher, d.s.b., much more desirably, in crystalline powder or crystal with a neotrehalose content of 90 w/w % or higher, d.s.b. The process comprising first exposing lactoneotrehalose to β-galactosidase, then collecting it, which is disclosed in Japan Patent Kokai No.179, 790/92 by the same applicant, is very advantageous in an industrial-scale production because it can be easily scaled up.

The α-glucosyl saccharide can be arbitrarily chosen among usual amylaceous substances, for example, gelatinized starch, liquefied starch, solubilized starch, partial starch hydrolysate and saccharide-transferred starch product. The most advantageous saccharide-transferring enzyme is cyclomaltodextrin glucanotransferase (EC 2.4.1.19) but α-amylase (EC 3.2.1.1) can be used if necessary.

In case of using cyclomaltodextrin glucanotransferase, conventional enzymes from microorganisms such as those of the genera Bacillus and Klebsiella are arbitrarily chosen. Enzymes from microorganisms of the genus Bacillus, in particular, those of saccharifying type, are feasible as α-amylase.

Any saccharide-transfer reaction can be used as long as it yields the non-reducing oligosaccharide of the present invention. For example, in the case of using cyclomaltodextrin glucanotransferase and α-amylase, those are allowed to react on an aqueous solution containing neotrehalose along with an amylaceous substance such as partial starch hydrolysate to transfer α-glucosyl groups from the substance to the glucosyl groups in neotrehalose, thus obtaining the non-reducing oligosaccharide of the present invention. In this case, appropriate weight ratios of amylaceous substances against neotrehalose are usually within the range of 0.1 to 100, desirably, 0.2 to 20.

The enzymatic reactions as described above are usually carried out at a temperature of 20°–80° C. and a pH of 3–9, and, in such a reaction, enzymes and microorganisms containing the same may be immobilized and then repeatedly used. Among the aforementioned saccharide-transfer reactions, the reaction using cyclomaltodextrin glucanotransferase is generally preferable, because of allowing the use of cheaper α-glucosyl saccharides as a saccharide donor and the elevated production yield of a non-reducing oligosaccharide with neotrehalose structure represented by the general formula of β-D-oligoglucosyl α-D-glucoside, α-D-oligoglucosyl β-D-glucoside or β-D-oligoglucosyl α-D-oligoglucoside. In particular, the use of cyclomaltodextrin glucanotransferase derived from Bacillus Stearothermophilus capable of acting at an elevated temperature is much more preferable from industrial viewpoint, because of allowing to suppress the retrogradation of amylaceous substances and microbial contamination in reaction mixtures and to accelerate the enzymatic reaction. In this case, usually, an aqueous solution which contains neotrehalose along with gelatinized starch, liquefied starch, partial starch hydrolysate with a dextrose equivalent (DE) of 1–50 and starch products such as amylodextrin and cyclodextrin is exposed to 0.1 units/g starch product or more, desirably, 1–100 units/g starch product, d.s.b., of cyclomaltodextrin glucanotransferase for 1–100 hours, desirably, for 4–70 hours so that non-reducing oligosaccharides where one or more α-glucosyl groups are bound to either or both of the glucosyl groups in neotrehalose, for example, β-maltosyl α-glucoside, α-maltosyl β-glucoside, β-maltosyl α-maltoside (α-maltosyl β-maltoside), β-maltotriosyl α-glucoside, α-maltotriosyl β-glucoside, β-maltotriosyl α-maltoside, α-maltotriosyl β-maltoside, β-maltotriosyl α-maltotrioside (α-maltotriosyl β-maltotrioside), β-maltotetraosyl α-glucoside, α-maltotetraosyl β-glucoside, β-maltotetraosyl α-maltoside, α-maltotetraosyl β-maltoside, β-maltotetraosyl α-maltotrioside, α-maltotetraosyl β-maltotrioside, β-maltotetraosyl α-maltotetraoside (α-maltotetraosyl β-maltotetraoside), β-maltopentaosyl α-glucoside, α-maltopentaosyl β-glucoside, β-maltopentaosyl α-maltoside, α-maltopentaosyl β-maltoside, β-maltopentaosyl α-maltotrioside, α-maltopentaosyl β-maltotrioside, β-maltopentaosyl α-maltotetraoside, α-maltopentaosyl β-maltoteraoside, and β-maltopentaosyl α-maltopentaoside (α-maltopentaosyl β-maltopentaoside) are formed, and followed by recovering them. If necessary, these can be further exposed to β-amylase (EC 3.2.1.2) to accumulate as predominant products eight types of non-reducing oligosaccharides which are β-maltosyl α-glucoside, α-maltosyl β-glucoside, β-maltosyl α-maltoside (α-maltosyl β-maltoside), β-maltotriosyl α-glucoside, α-maltotriosyl β-glucoside, β-maltotriosyl α-maltoside, α-maltotriosyl β-maltoside and β-maltotriosyl α-maltotrioside (α-maltotriosyl β-maltotrioside), followed by recovering them.

As mentioned above, solutions containing usually 5–40 w/w %, d.s.b., of a non-reducing tetra or higher oligosaccharide with neotrehalose structure which is formed by the saccharide-transfer reaction or in combination with hydrolysis can be used in liquid form after filtration and purification, or in syrup form after concentration, and further can be used arbitrarily in solid form after dehydration such as spray or vacuum drying.

Generally to utilize the properties of relatively lower molecular weight of non-reducing oligosaccharides with neotrehalose structure, solutions containing tri-, tetra- and penta-saccharides, which are obtainable after completion of saccharide-transfer reaction and then hydrolysis, are subjected to further separation and purification into tri-, tetra- and penta-saccharide rich products. For such a separation and purification, usual methods which can separate and remove contaminant saccharides by yeast fermentation, membrane filtration, fractional sedimentation and/or column chromatography are arbitrarily chosen. In particular, column chromatography using strongly-acidic cation exchanger as disclosed in Japan Patent Kokai No.23,799/83 and No.72, 598/83 is favorably feasible in the removal of concomitant saccharide so as to collect fractions which are rich in non-reducing tetra-, penta- and hexa-saccharides. In such a chromatography, fixed bed method, moving bed method and simulated moving bed method are arbitrarily practicable. If necessary, these tetra-, penta- and hexa-saccharides can be separately collected.

The non-reducing oligosaccharide with neotrehatose structure of this invention exhibits not reducing ability but very stability, and is tasteless or low in sweetness and less or not susceptible to crystallization. In addition the non-reducing oligosaccharide of this invention is effective as calorie source because of its susceptibility to digesting enzymes and assimilability in vivo upon oral intake. Further the oligosaccharide of this invention is useful as saccharide sweetener material having a reduced sweetening power and cariogenicity because of its substantial no fermentability by cariogenic microorganisms. Additionally, the oligosaccharide of this invention is chemically stable so that it can be used along with amino acids, oligopeptides and proteins which readily cause browning reaction with saccharides. Further the oligosaccharide of this invention stabilizes biologically-active substances which deteriorate readily their activity, and further have properties of controlling osmotic pressure, imparting shapes and gloss, holding an appropriate moisture-retaining activity content and viscosity, preventing crystallization of other saccharides, exhibiting less fermentability, and preventing retrogradation of amylaceous substances.

These properties of non-reducing oligosaccharide with neotrehalose structure in the molecule are favorably utilizable in the production of food products including beverages, foods, feeds as well as pet foods, and also in the production of cosmetics and pharmaceuticals.

Non-reducing oligosaccharides with neotrehalose structure and a relatively-low molecular weight according to this invention are low in sweetening power, however, utilizable intact as sweetening seasoning. Such a non-reducing oligosaccharide can be used together with an appropriate amount of one or more sweeteners, for example, powdered starch syrup, glucose, fructose, maltose, sucrose, isomerized sugar, honey, maple sugar, erythritol, sorbitol, dihydrochalcone, stevioside, α-glycosyl stevioside, rebaudioside, glycyrrhizin, L-aspartyl-L-phenylalanine methyl ester, saccharin, glycine and alanine, as well as along with a filler such as dextrin, starch and lactose, if necessary.

Powdered non-reducing oligosaccharides with neotrehalose structure according to this invention can be used intact, or, if necessary, shaped into granule, globe, short rod, plate, cube or tablet form after mixing them with other filler, vehicle or binder.

Further the non-reducing oligosaccharide with neotrehalose structure according to this invention is favorably usable to sweeten foods and beverages in general as well as to improve their tastes and qualities because its tastelessness or low sweetness well blends with substances which have other types of tastes such as soda, salty, astringent, delicious and bitter tastes, and further because it is highly acid- and heat-resistant. For example, the non-reducing oligosaccharide of this invention is favorably utilizable in various seasonings such as soy sauce, soy sauce powder, miso, miso powder, "moromi (unrefined soy sauce)", "hishio (miso sauce mixed with salted vegetables)", "furikake (fish or laver flour)", mayonnaise, dressing, vinegar, "sanbai-zu (sauce mixing sake, soy and vinegar)", "funmatsu-sushi-su (powdered vinegar for sushi)", "chuka-no-moto (Chinese taste seasoning)", "tentsuyu (soup for tenpura)", "mentsuyu (soup for Japanese-style noodles)", sauce, ketchup, "yakiniku-no-tare (soup for grilled meat)", curry roux, stew premix, soup premix, "dashi-no-moto (dried bonito taste seasoning)", nucleic acid seasoning, mixed seasoning, "mirin (heavily sweetened sake)", "shin-mirin (synthetic mirin)", table sugar and coffee sugar.

In addition, the non-reducing oligosaccharide of this invention is favorably usable to sweeten, for example, Japanese-style confectioneries such as "senbei (rice crackers)", "arare (glutinous rice crackers)", "okoshi (millet and rice crackers)", rice cake, "manju (bun with a bean-jam filling)", "uiro (sweet rice jelly)", "an (bean jam)", "yokan (sweet jelly of beans)", "mizu-yokan (soft adzuki-bean jelly)", "kingyoku", jelly, castellan and "amedama (Japanese-style toffee)"; Western-style confectioneries such as bun, biscuit, cracker, cookie, pie, pudding, butter cream, custard cream, cream puff, waffle, sponge cake, doughnut, chocolate, chewing gum, caramel and candy; frozen desserts such as ice cream and sherbet; syrups such as those for fruit preserve end "kaki-gori (shaved ice)"; spreads and pastes such as flour paste, peanut paste and fruit paste; processed fruits and vegetables such as jam, marmalade, syrup-preserved fruit and crystallized fruit; pickled products such as "fukujin-zuke (sliced vegetables pickled in soy sauce)", "bettara-zuke (fresh radish pickles)", "senmai-zuke" and "rakkyo-zuke (pickled shallots)"; premixes for pickled products such as "takuan-zuke-no-moto" and "hakusai-zuke-no-moto"; meat products such as ham and sausage; fish meat products such as fish meat ham, fish meat sausage, "kamaboko (boiled fish paste)", "chikuwa (bamboo wheels shaped kamaboko)" and "tenpure (deep fried foods)"; relishes such as "uni-no-shiokara (salted guts of sea urchin )", "ika-no-shiokara ( salted guts of squid )", "su-konbu", "saki-surume" and "fugu-no-mirinboshi"; "tsukudani (food boiled down in soy sauce)" such as those of "nori (dried seaweed)", "sansai (mountain vegetables)", "surume (dried squid)", small fish and shellfish; daily dishes such as "nimame (cooked beans)", potato salad and "konbu-maki (tangle roll)"; milk products; bottled and canned products such as those of meat, fish meat, fruit and vegetable; alcoholic drinks such as synthetic sake, liqueur, wine and whisky; beverages such as coffee, tea, cocoa, juice, carbonated beverage, lactic acid beverage and lactobacillus beverage; premixes and instant foodstuffs such as pudding premix, hot cake premix, "sokuseki-shiruko (pre-mix of adzuki-bean soup with rice cake)" and instant soup; baby foods; diet foodstuffs; and nutrient beverage, as well as to improve their tastes and qualities.

Further the non-reducing oligosaccharide of this invention can be used in feeds and pet foods for domestic animals and poultries including honey bee, silkworm and fish so as to improve their taste qualities. Still further the non-reducing oligosaccharide of this invention is favorably usable as sweetener for orally-usable products in solid, paste or liquid form including cosmetics and pharmaceuticals such as cigarette, dentifrice, lipstick, lip cream, internal medicine, troche, cod-liver oil drop, oral refreshing agent, cachou and gargle, in addition, usable as taste quality improving agent, taste masking agent and quality improving agent.

Further the non-reducing oligosaccharide with neotrehalose structure according to this invention is favorably utilizable as stabilizer, osmosis-controlling agent, vehicle, moisture-controlling agent, viscosity-controlling agent and quality-improving agent in the production of cosmetics, for example, soap, skin cream, body shampoo, hair cream, lip cream, skin refining agent and hair restorer.

The non-reducing oligosaccharide of this invention is also favorably usable in the production of pharmaceuticals as stabilizer for activities or active ingredients in biologically-active substances, for example, cytokines including interferon-$\alpha$, interferon-$\beta$, interraton-$\gamma$, tumor necrosis factor-$\alpha$, tumor necrosis factor-$\beta$, macrophage-migration inhibitory factor, colony stimulating factor, transfer factor and interleukin 2; hormones such as insulin, growth hormone, prolactin, erythropoietin and follicle-stimulating hormone; vaccines such as BCG vaccine, Japanese encephalitis vaccine, measles vaccine, poliomyelitis vaccine, vaccinia virus vaccine, tetanus toxoid, trimeresurus flavoviridis antivenom and human immunoglobulin; antibiotics such as penicillin, erythromycin, chloramphenicol, tetracycline, streptomycin and kanamycin sulfate; vitamins such as thiamine, riboflavin, L-ascorbic acid, cod-liver oil, carotenoid, ergosterol and tocopherol; enzymes such as lipase, elastase, urokinase, protease and glucanase; extracts such as ginseng extract, snapping turtle extract, chlorella extract, propolls extract and royal jelly; and viable microorganisms such as virus, lactobacillus, bifidobacterium and yeast. In addition, the oligosaccharide of this invention is usable as osmosis-controlling agent, vehicle, intubation feeding, sugar coating agent and syrup agent in the production of pharmaceuticals. For incorporating the non-reducing oligosaccharide with neotrehalose structure of this invention in the aforementioned composition including foods, beverages, cosmetics, pharmaceuticals and shaped bodies, usual methods, for example, mixing, kneading, dissolving, melting, soaking, permeating, spreading, applying, coating, spraying, injecting and solidifying are arbitrarily used before completion of their processing. The amount of the non-reducing oligosaccharide with neotrehalose structure to be incorporated is up to a level which allows said non-reducing oligosaccharide to exhibit its properties, usually, 0.5 w/w % or more, desirably, one w/w % or more in products.

The following experiments will explain in detail the non-reducing oligosaccharide with neotrehalose structure of this invention.

EXPERIMENT

Production of Non-Reducing Oligosaccharide with Neotrehalose Structure and its Physicochemical Properties Experiment 1

Production of Neotrehalose

Experiment 1-1

Preparation of Lactoneotrehalose

Fifty parts by weight of lactose commercially available and "PINE-DEX #1", a dextrin product (DE 8) commercialized by Matsutani Chemical Ind., Co., Ltd., Kyoto, Japan, were dissolved in 150 parts by weight of water while heating and the resultant solution was adjusted to 60° C. and pH 6.0, added with a cyclomaltodextrin glucanotransferase from *Bacillus stearothermophilus*, commercialized by Hayashibara Biochemical Laboratories, Inc., Okayama, Japan, in an amount of 300 units/g dextrin, reacted for 20 hours and heated at 100° C. for 30 minutes to inactivate the enzyme. The solution was then adjusted to 55° C. and pH 5.0, mixed with glucoamylase, commercialized by Nagase Biochemicals Ltd., Kyoto, Japan, in an amount of 15 units/g partial starch hydrolysate, reacted for 16 hours and successively heated at 100° C. for 15 minutes to inactivate the enzyme. The resultant solution contained about 24 w/w % lactoneotrehalose, d.s.b.

Experiment 1-2

Production of Neotrehalose

The lactoneotrehalose-contained solution obtained in Experiment 1-1 was mixed with "Kactase LP", $\beta$-galactosidase commercialized by K.I Chemical Industrial Co., Ltd., Shizuoka, Japan, in an amount of 10 units/g substrate of the solution obtained in Experiment 1-1, reacted at 60° C. for 20 hours and then heated at 100° C. for 10 minutes to inactivate the enzyme. The resultant solution contained about 16 w/w % neotrehalose, d.s.b. According to usual manners, the solution thus obtained was decoionized with an activated charcoal, desalted with ion-exchange resins and concentrated to give a concentration of about 60 w/w %, d.s.b., and the solution thus concentrated was charged to a stainless-steel column prepacked with "CG6000, $Na^+$ form", a strongly-acidic cation exchange resin commercialized by Japan Organo, Co., Ltd., Tokyo, Japan, with 60° C. water and at SV 0.4 for fractionation, and followed by recovering neotrehalose-rich fractions. The fractions contained about 88 w/w % neotrehalose, d.s.b., was concentrated into a solution having a concentration of about 75 w/w %, and then fed in a crystallizer, mixed with about 2 w/w % hydrous crystalline neotrehalose as a seed crystal and gradually mixed to form crystal, and the resultant massecuite was separated to obtain a crystal which was then washed by spraying with a small amount of water to obtain a high-purity crystal.

Experiment 2

Preparation of Non-Reducing Oligosaccharide with Neotrehalose Structure

Fifty parts by weight of neotrehalose prepared by the method in Experiment 1 and an α-cyclodextrin product, commercialized by Hayashibara Biochemical Laboratories, Inc., Okayama, Japan, were dissolved in 150 parts by weight of water and the resultant solution was adjusted to 55° C. and pH 5.5, mixed with a cyclomaltodextrin glucanotransferase from *Bacillus stearothermophilus*, commercialized by Hayashibara Biochemical Laboratories, Inc., Okayams, Japan, in an amount of 50 units/g α-cyclodextrin, reacted for 35 hours, and heated at 100° C. for 30 minutes to inactivate the enzyme. The solution was then adjusted to 40° C. and pH 5.5, added with "β-amylase #1500", β-amylase commercialized by Nagase Biochemicals Ltd., Kyoto, Japan, in an amount of 20 units/g partial starch hydrolysate, reacted for 18 hours and then heated at 100° C. for 15 minutes to inactivate the enzyme. The resultant solution contained, as β-D-oligoglucosyl α-D-glucoside, α-D-oligoglucosyl β-D-glucoside and β-D-oligoglucosyl α-D-oligoglucoside of this invention, "Substances 1", "Substance 2", "Substance 3", "Substance 4", "Substance 5", "Substance 6", "Substance 7" and "Substance 8" in an amount of about 12 w/w %, 13 w/w 4, 10 w/w 4, 8 w/w %, 11 w/w %, 6 w/w %, 7 w/w % and 3 w/w %, d.s.b., respectively. The solution was decolored with an activated charcoal, desalted with ion-exchangers ($H^+$- and $OH^-$-form) and concentrated to give a concentration of about 45 w/w %, d.s.b., and subjected to column chromatography to collect fractions which were rich in Substances 1, 2, 3, 4 and 5. As a resin for the column chromatography, "XT-1016, $Na^+$ form", a strongly-acid cation ion-exchange resin commercialized by Japan Organo Co., Ltd., Tokyo, Japan, was used and packed in an aqueous suspension form in 4 jacketed stainless-steel columns, having an inner diameter of 5.4 cm and a gel-bed depth of 5 m each, which were then cascaded in series to give a total gel-bed depth of about 20 m. While keeping the inner column temperature at 55° C., the columns were charged with 5 v/v % material saccharide solution and then applied with 55° C. water at SV 0.3 for fractionation, followed by recovering fractions which were rich in Substances 1, 2, 3, 4 and 5. The fractions of Substances 1, 2, 3, 4 and 5 were further applied to a preparative liquid chromatography prepacked with using "YMC-Pack R-355-15, an octadecyl silica gel commercialized by YMC Co., Ltd., Kyoto, Japan, as a column for the preparative liquid chromatography and also water as eluent, and fractions containing Substances 1, 2, 3, 4 and 5 in an amount of about 96 w/w % or higher, d.s.b., were collected, lyophilized and pulverized to obtain high-purity Substances 1, 2, 3, 4 and 5.

Experiment 3

Physicochemical Properties of Non-Reducing Oligosaccharide with Neotrehalose Structure Using high-purity Substances 1, 2, 3, 4 and 5 prepared by the method in Experiment 2, the following physicochemical properties were determined.

(1) Molecular weight

Substance 1 504.4

Substance 2 504.4

Substance 3 666.6

Substance 4 666.6

Substance 5 666.6

(2) Molecular formula

Substance 1 $C_{18}H_{32}O_{16}$

Substance 2 $C_{18}H_{32}O_{16}$

Substance 3 $C_{24}H_{42}O_{21}$

Substance 4 $C_{24}H_{42}O_{21}$

Substance 5 $C_{24}H_{42}O_{21}$ (3) Ultraviolet absorption

These five substances exhibited no characteristic absorption.

(4) Coloring reaction

These five substances colored into Green upon the anthrone-sulfuric acid reaction but were negative to both the Fehling's reaction and iodine reaction.

(5) Structure (a) Upon hydrolysis by 1N sulfuric acid, Substances 1 and 2 formed three moles of D-glucose from one mole of the standard substances, and Substances 3, 4 and 5 formed four moles of D-glucose from one mole of the standard substances.

(b) When exposed to glucoamylase, Substances 1 and 2 formed one mole of glucose and of neotrehalose, and Substances 3, 4 and 5 formed two moles of glucose and one mole of neotrehalose.

(c) When dissolved in heavy water, using by GSX-400 type nuclear resonance apparatus produced by Japan Electron Optics Laboratory Co., Ltd. and as an inner standard substance, TSP (($CH_3)_3Si(CD_3)_2CO_2Na$), carbon nuclear resonance analysis ($^{13}C$-NMR) gave distinct eighteen $^{13}C$ signals for Substances 1 and 2 and distinct twenty four $^{13}C$ signals for Substances 3, 4 and 5. In accordance with the chemical shifts reported in Klaus Bock et al., *Advances in Carbohydrate Chemistry and Biochemistry*, Vol.42, pp.192–225 (1984) for neotrehalose, maltose and maltotriose as standard substances, and by assigning these carbon atoms as Table 1, it was suggested that Substance 1 had a structure represented by O-α-D-glucopyranosyl-(1→4) -β-D-glucopyranosyl α-D-glucopyranoside, Substance 2 had a structure represented by O-α-D-glucopyranosyl-(1→4)-α-D-glucopyranosyl β-D-glucopyranoside, Substance 3 had a structure represented by O-α-D-glucopyranosyl-(1→4)-O-α-D-glucopyranosyl-(1→4)-β-D-glucopyranosyl α-D- glucopyranoside, Substance 4 had a structure represented by O-α-D-gluco- pyranosyl-(1→4)-O-α-D-glucopyranosyl-(1→4)-α-D-glucopyranosyl β-D-glucopyranoside and Substance 5 had a structure represented by O-α-D-glucopyranosyl-(1→4)-β-D-glucopyranosyl α-D-maltoside.

Based on the above results, the structure of Substances 1, 2, 3, 4 and 5 can be represented by Chemical formulae 1, 2, 3, 4 and 5. Because of these structures, Substances 1, 2, 3, 4 and 5 were designated as β-maltosyl α-glucoside, α-maltosyl β-glucoside, β-maltotriosyl α-glucoside, α-maltotriosyl β-glucoside and β-maltosyl α-maltoside, respectively.

Chemical formula 1:

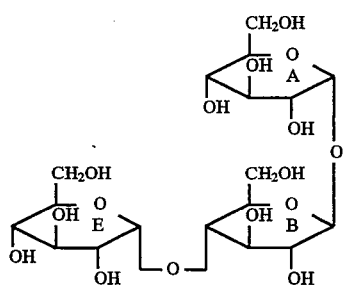

Chemical formula 2:

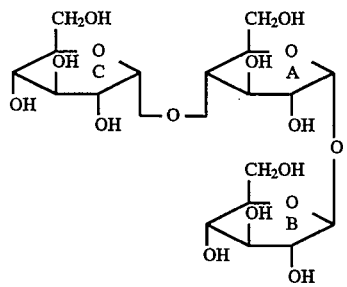

TABLE 1

| GR | Carbon No. | S-1 | S-2 | S-3 | S-4 | S-5 |
|---|---|---|---|---|---|---|
|   |   | (ppm) | | | | |
| D | C-1 |  |  |  | 102.6 |  |
|   | C-2 |  |  |  | 74.6 |  |
|   | C-3 |  |  |  | 75.7 |  |
|   | C-4 |  |  |  | 72.1 |  |
|   | C-5 |  |  |  | 75.5 |  |
|   | C-6 |  |  |  | 63.3 |  |
| C | C-1 |  | 102.4 |  | 102.3 | 102.4 |
|   | C-2 |  | 74.6 |  | 74.4 | 74.6 |
|   | C-3 |  | 75.7 |  | 76.1 | 75.7 |
|   | C-4 |  | 72.2 |  | 79.6 | 72.2 |
|   | C-5 |  | 75.5 |  | 74.0 | 75.5 |
|   | C-6 |  | 63.6 |  | 63.3 | 63.3 |
| A | C-1 | 103.0 | 102.9 | 103.0 | 102.9 | 102.8 |
|   | C-2 | 74.3 | 74.1 | 74.3 | 74.1 | 74.1 |
|   | C-3 | 75.7 | 76.1 | 75.6 | 76.1 | 76.1 |
|   | C-4 | 72.2 | 79.4 | 72.1 | 79.6 | 79.4 |
|   | C-5 | 75.5 | 74.0 | 75.5 | 74.0 | 74.0 |
|   | C-6 | 63.3 | 63.2 | 63.3 | 63.2 | 63.2 |
| B | C-1 | 105.6 | 105.8 | 105.6 | 105.8 | 105.6 |
|   | C-2 | 75.8 | 75.9 | 75.8 | 75.9 | 75.8 |
|   | C-3 | 78.7 | 79.0 | 78.6 | 79.0 | 78.7 |
|   | C-4 | 79.4 | 72.2 | 79.6 | 72.2 | 79.4 |

TABLE 1-continued

| GR | Carbon No. | S-1 | S-2 | S-3 | S-4 | S-5 |
|---|---|---|---|---|---|---|
|   |   | (ppm) | | | | |
|   | C-5 | 77.6 | 78.2 | 77.6 | 78.2 | 77.6 |
|   | C-6 | 63.5 | 63.4 | 63.4 | 63.4 | 63.5 |
| E | C-1 |  | 102.4 |  | 102.3 | 102.4 |
|   | C-2 |  | 74.5 |  | 74.3 | 74.5 |
|   | C-3 |  | 75.7 |  | 76.1 | 75.7 |
|   | C-4 |  | 72.2 |  | 79.6 | 72.2 |
|   | C-5 |  | 75.5 |  | 74.0 | 75.5 |
|   | C-6 |  | 63.3 |  | 63.3 | 63.3 |
| F | C-1 |  |  |  | 102.6 |  |
|   | C-2 |  |  |  | 74.6 |  |
|   | C-3 |  |  |  | 75.7 |  |
|   | C-4 |  |  |  | 72.2 |  |
|   | C-5 |  |  |  | 75.5 |  |
|   | C-6 |  |  |  | 63.3 |  |

GR: Glucose residue, S-1: Substance 1, S-2: Substance 2, S-3: Substance 3, S-4: Substance 4, S-5: Substance 5

Chemical formula 3:

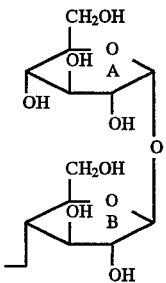
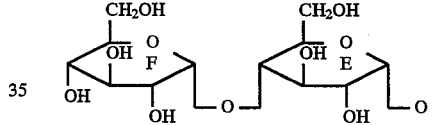

Chemical formula 4:

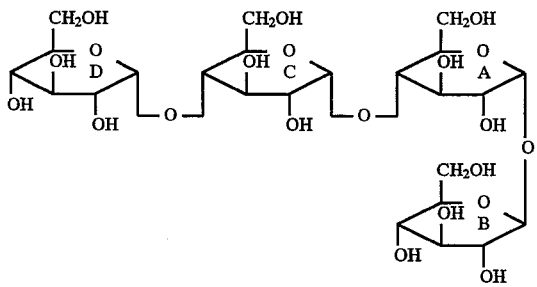

Chemical formula 5:

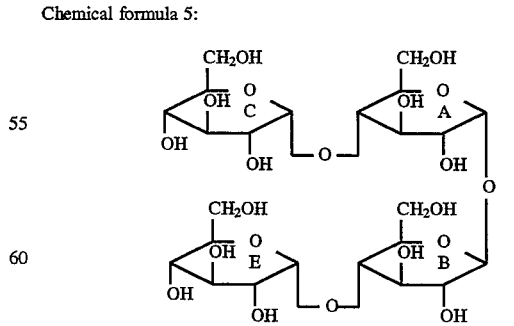

Thus, the present non-reducing oligosaccharide including these substances can be represented by the following general formula:

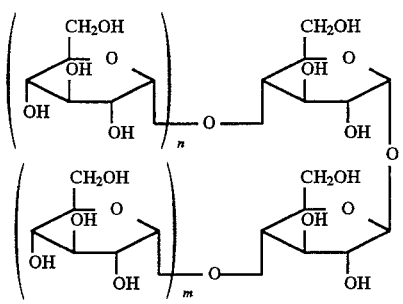

where "n" and "m" are 0 or more integers, and their total number (n+m) is at least 1.

Experiment 4

Acute Toxicity

High-purity β-maltosyl α-glucoside, α-maltosyl β-glucoside, β-maltotriosyl α-glucoside, α-maltotriosyl β-glucoside and β-maltosyl α-maltoside prepared by the method in Experiment 2 were tested for acute toxicity in mice upon oral administration. As the result, β-maltosyl α-glucoside, α-maltosyl β-glucoside, β-maltotriosyl α-glucoside, α-maltotriosyl β-glucoside and β-maltosyl α-maltoside were found to be less toxic and no death was observed with their maximum administrable dose. These suggest that their $LD_{50}$ would be briefly 50 g/kg or higher.

The following Example A and Example B will illustrate the production of non-reducing oligosaccharide with neotrehalose structure represented by the general formula of β-D-oligoglucosyl α-D-glucoside, α-D-oligoglucosyl β-D-glucoside or β-D-oligoglucosyl α-D-oligoglucoside and several uses of the same respectively.

Example A-1

One part by weight of neotrehalose prepared by the method in Experiment 1 and two parts by weight of "PINE-DEX #4", a dextrin product (DE 18) commercialized by Matsutani Chemical Ind., Co., Ltd., Kyoto, Japan, were dissolved in 3.7 parts by weight of water while heating and the resultant solution was adjusted to 60° C. and pH 5.6, added with cyclomaltodextrin glucanotransferase from *Bacillus stearothermophilus*, commercialized by Hayashibara Biochemical Laboratories, Inc., Okayama, Japan, in an amount of 30 units/g dextrin, reacted for 20 hours and followed by heating to inactivate the enzyme. Thereafter the solution was decolored with activated carbon, desalted with ion-exchangers ($H^+$- and $OH^-$-form) and concentrated in usual manner to obtain 75 w/w % syrup in the yield of about 92 w/w % d.s.b.

The product, which contains about 65 w/w % non-reducing oligosaccharide, d.s.b., such as β-maltosyl α-glucoside, α-maltosyl β-glucoside, β-maltotriosyl α-glucoside, α-maltotriosyl β-glucoside and β-maltosyl α-maltoside, d.s.b., has a reduced sweetness, appropriate viscosity and moisture-retaining activity which render the product very useful in a variety of compositions including foods, beverages, cosmetics and pharmaceuticals.

Example A-2

One part by weight of neotrehalose prepared by the method in Experiment 1 and 1.5 parts by weight of α-cyclodextrin, commercialized by Hayashibara Biochemical Laboratories, Inc., Okayama, Japan, were dissolved in 4 parts by weight of water while heating and the resultant solution was adjusted to 65° C. and pH 5.6, added with the same type of cyclomaltodextrin glucanotransferase as used in Example A-1 in an amount of 20 units/g α-cyclodextrin, reacted for 24 hours and heated to inactivate the enzyme. The solution was then adjusted to 55° C. and pH 5.6, added with 20 units/g solid of "β-amylase #1500", β-amylase commercialized by Nagase Biochemicals Ltd., Kyoto, Japan, reacted for 16 and heated to inactivate the enzyme. Thereafter the solution was purified and concentrated similarly as in Example A-1 to obtain 75 w/w % syrup in the yield of about 93%, d.s.b.

The product, which contains about 50 w/w % non-reducing oligosaccharide, d.s.b., such as β-maltosyl α-glucoside, α-maltosyl β-glucoside, β-maltotriosyl α-glucoside, α-maltotriosyl β-glucoside and β-maltosyl α-maltoside, d.s.b., has a reduced sweetness, appropriate viscosity and moisture-retaining activity as the product in Example A-1 which renders the product very useful in a variety of compositions including foods, beverages, cosmetics and pharmaceuticals.

Example A-3

A starch suspension with 20 w/w % concentration was added with "Termamyl 60L", α-amylase commercialized by Novo Nordisk Bioindustry, Copenhagen, Denmark, in an amount of 0.015 w/w % with respect to starch solid, liquefied at 95°–100° C. and heated to inactivate the enzyme, thus obtaining a liquefied starch solution with DE 3. The solution was added with neotrehalose prepared by the method in Example 1 in the same amount as that of amylaceous substance, d.s.b., adjusted to 55° C. and pH 5.3, added with 250 units/g starch of an isoamylase, commercialized by Hayashibara Biochemical Laboratories, Inc., Okayama, Japan, and 30 units/g starch of the same type of cyclomaltodextrin glucanotransferase as used in Example A-1, reacted for 40 hours and heated to inactivate the enzymes. The solution was then diluted to about 25 w/w % by addition of water, adjusted to 55° C. and pH 5.3, added with 20 units/g solid of β-amylase, reacted for 16 hours and heated to inactivate the enzyme. Thereafter the solution was purified and concentrated similarly as in Example A-1 to obtain 75 w/w % syrup in the yield of about 90 w/w %, d.s.b.

The product, which contains about 45 w/w % non-reducing oligosaccharide such as β-maltosyl α-glucoside, α-maltosyl β-glucoside, β-maltotriosyl α-glucoside, a-maltotriosyl β-glucoside and β-maltosyl a-maltoside, d.s.b., has a reduced sweetness, appropriate viscosity and moisture-retaining activity as the product in Example A-1 which render the product very useful in a variety of compositions including foods, beverages, cosmetics and pharmaceuticals.

Example A-4

A material saccharide solution which contained β-maltosyl α-glucoside, α-maltosyl β-glucoside, β-maltotriosyl α-glucoside, α-maltotriosyl β-glucoside and β-maltosyl α-maltoside prepared by the method in Example A-2 was concentrated to about 45 w/w %. To heighten the contents of non-reducing oligosaccharide such as β-maltosyl α-glucoside, α-maltosyl β-glucoside, β-maltotriosyl α-glucoside, α-maltotriosyl β-glucoside and β-maltosyl α-maltoside, the solution was chromatographed similarly as in Experiment 1 except that the ion-exchange resin for fractionation was replaced with "Dowex 50W-X4, $Ca^{2+}$- form", a strongly-acidic action ion-exchange resin commercialized by the Dow Chemical Co., Midland, Mich., USA, and fractions which were rich in such a non-reducing oligosaccharide as β-maltosyl α-glucoside, α-maltosyl β-glucoside, β-maltotriosyl α-glucoside, α-maltotriosyl β-glucoside and β-maltosyl α-maltoside were collected.

The syrup contains about 80 w/w % high-purity non-reducing oligosaccharide such as β-maltosyl α-glucoside, α-maltosyl β-glucoside, β-maltotriosyl α-glucoside, α-maltotriosyl β-glucoside and β-maltosyl α-maltoside, d.s.b.

Example A-5

A syrupy material saccharide solution which contained a high-purity β-maltosyl α-glucoside, α-maltosyl β-glucoside, β-maltotriosyl α-glucoside, α-maltotriosyl β-glucoside and β-maltosyl α-maltoside prepared by the method in Example A-4 was concentrated to about 50 w/w %. The solution was subjected to a preparative liquid chromatography pre-packed with octadecyl silica gel similarly as in Experiment 2, and fractions which were rich in β-maltosyl α-glucoside, α-maltosyl β-glucoside, β-maltotriosyl α-glucoside, α-maltotriosyl β-glucoside and β-maltosyl α-maltoside were collected.

The syrups contain about 97 w/w % high-purity β-maltosyl α-glucoside, α-maltosyl β-glucoside, β-maltotriosyl α-glucoside, α-maltotriosyl β-glucoside and β-maltosyl α-maltoside, d.s.b.

Example A-6

A high-purity syrup of β-maltosyl α-glucoside, α-maltosyl β-glucoside, β-maltotriosyl α-glucoside, α-maltotriosyl β-glucoside and β-maltosyl α-maltoside prepared by the method in Example A-5, respectively, was lyophilized for 24 hours. The obtained dried product was applied to pulverizer so as to obtain a powder with a moisture content of about 0.9 w/w % in the yield of about 95 w/w %, d.s.b.

Example A-7

A high-purity syrup of non-reducing oligosaccharide such as β-maltosyl α-glucoside, α-maltosyl β-glucoside, β-maltotriosyl α-glucoside, α-maltotriosyl β-glucoside and β-maltosyl α-maltoside prepared by the method in Example A-4 was lyophilized for 24 hours. The resultant product thus obtained and dried was applied to pulverizer to obtain a powder with a moisture content of about 1.1 w/w % in the yield of about 96 w/w %, d.s.b.

Example B-1

Granular Sweetener

One part by weight of a high-purity α-maltosyl β-glucoside powder obtained by the method in Example A-6 and 0.05 parts by weight of "α G Sweet", α-glycosyl stevioside commercialized by Toyo Sugar Refining Co., Ltd., Tokyo, Japan, were mixed to homogeneity and the mixture was fed to granulator to obtain a granular sweetener.

The sweetener has a superior taste quality and about two-fold stronger sweetening power and the calorie in terms of sweetening power is about one half in comparison with sucrose.

The sweetener is suitable as a low-calory sweetener to sweeten low-calorie foods and beverages for those having obesity or diabetes whose calorie intakes are restricted.

Further the sweetener is also suitable to sweeten foods and beverages which are directed to suppress dental caries because it is less in acid and insoluble glucan production by cariogenic microorganisms.

Example B-2

Hard Candy

One hundred parts by weight of 55 w/w % sucrose solution and thirty parts by weight of a syrup containing non-reducing oligosaccharides obtained by the method in Example A-1 were mixed while heating, and the mixture was concentrated to a moisture content lower than 2 w/w % by heating in vacuo, added with 1 parts by weight of citric acid and appropriate amounts of lemon flavor and coloring agent and shaped in usual manner.

The product is a high-quality hard candy which is crisp, superior in taste quality and free of crystallization of sucrose.

Example B-3

Strawberry Jam

One hundred and fifty parts by weight of fresh strawberry, 60 parts by weight of sucrose, 20 parts by weight of maltose, 40 parts by weight of a syrup containing non-reducing oligosaccharides obtained by the method in Example A-4, 5 parts by weight of pectin and 1 part by weight of citric acid were boiled down in a pot and the resultant was bottled.

The product is a jam, having a superior flavor and color.

Example B-4

Lactic Acid Drink

Ten parts by weight of defatted milk was pasteurized at 80° C. for 20 minutes, cooled to 40° C., added with 0.3 parts by weight of starter and fermented at 37° C. for 10 hours. The resultant was homogenized, added with 4 parts by weight of a powder containing α-maltosyl β-glucoside obtained by the method in Example A-6, one part by weight of sucrose and 2 parts by weight of isomerized sugar and the mixture was pasteurized by keeping it at 70° C. Thereafter the mixture was cooled, added with an appropriate amount of flavoring agent and bottled.

The product is a high-quality lactic acid drink where flavor and sweetness well harmonized with sour taste.

Example B-5

Sweetened Condensed Milk

Three parts by weight of non-reducing oligosaccharides obtained by the method in Example A-3 and one part by weight of sucrose were dissolved in 100 parts by weight of fresh milk, and the resultant solution was sterilized by heating with plate heater, concentrated to about 70 w/w % and sterilely canned.

The product, having a mild sweetness and superior flavor, is favorably usable in baby foods and seasonings for fruits, coffee, cocoa and tea.

Example B-6

Powdered Juice

Thirty three parts by weight of spray-dried orange juice was mixed with 50 parts by weight of a high-purity β-maltosyl α-maltoside powder obtained by the method in Example A-6, 10 parts by weight of sucrose, 0.65 parts by weight of citric anhydride, 0.1 part by weight of malic acid, 0.1 part by weight of L-ascorbic acid, 0.1 part by weight of sodium citrate, 0.5 parts by weight of pullulan and an appropriate amount of powdered flavoring agent to homogeneity, pulverized into a fine powder, fed to fluidized-bed granulator and granulated at ventilation temperature of 40° C. for 30 minutes while spraying as a binder a syrup with high contents of non-reducing oligosaccharides obtained by the method in Example A-4, and divided into a prescribed amount and packaged.

The product is a powdered juice which has a natural fruit juice content of about 30 w/w %. The product is free of undesirable taste and smell, moisture intake and solidification, and very stable over an extended storage period.

Example B-7

Chocolate

Forty parts by weight of cacao paste, 10 parts by weight of cacao butter, 30 parts by weight of sucrose and 20 parts by weight of high-purity β-maltosyl α-maltoside powder obtained by the method in Example A-6 were mixed, and the resultant mixture was fed to refiner to reduce particle size, fed to conche and kneaded at 50° C. for 2 days. While such kneading, the mixture was added with 0.5 parts by weight of lecithin and sufficiently mixed and dispersed. Thereafter the mixture was adjusted to 31° C. with thermo-controller, poured in molds immediately before solidification of the butter, deaerated with vibrator and passed through 10° C. cooling tunnel over 20 minutes to complete solidification. The contents in the molds were then taken out and packaged.

The product, having no hygroscopicity, a superior color, gloss and texture, is very stable in inner structure and smoothly melted in the mouth to exhibit a gentle sweetness and mild flavor.

Example B-8

Chewing Gum

Three parts by weight of gum base was softened by heating, added with 4 parts by weight of sucrose and 3 parts by weight of high-purity α-maltotriosyl β-glucoside powder obtained by the method in Example A-6, mixed with appropriate amounts of flavoring and coloring agents, kneaded with roller, shaped and packaged in usual manner.

The product is a chewing gum having a superior texture, flavor and taste.

Example B-9

Custard Cream

One hundred parts by weight of corn starch, 100 parts by weight of a syrup containing non-reducing oligosaccharides obtained by the method in Example A-3, 80 parts by weight of maltose, 20 parts by weight of sucrose and one part by weight of sodium chloride were mixed to homogeneity, and the resultant mixture was added with 280 parts by weight of fresh egg, mixed by stirring, gradually added with 1,000 parts by weight of boiling milk, put on fire while stirring till the corn starch was gelatinized and the mixture wholly became semi-transparent, cooled, added with an appropriate amount of vanilla flavor, divided into prescribed amount and packaged.

The product has a smooth gloss, mild sweetness and delicious taste.

Example B-10

"Uiro-No-Moto" (Instant "Uiro")

Ninety parts by weight of rice powder was mixed with 20 parts by weight of corn starch, 120 parts by weight of high-purity non-reducing oligosaccharide powder obtained by the method in Example A-7 and 4 parts by weight of pullulan to homogeneity to obtain "uiro-no-moto". The "uiro-no-moto" was kneaded with appropriate amounts of "maccha (a green tea powder)" and water and the resultant mixture was divided in vessels and steamed for 60 minutes to obtain "maccha-uiro".

The product has a smooth gloss, good palatability and delicious taste, and also has a long shelf life because retrogradation of starch is effectively suppressed.

Example B-11

Milky Lotion

One half parts by weight of polyoxyethytene behenyl ether, 1 part by weight of polyoxyethylene sorbitol tetraoleate, 1 part by weight of oil-soluble glycerol monostearate, 0.5 parts by weight of behenyl alcohol, 1 part by weight of avocado oil, 3.5 parts by weight of a syrup containing high-purity β-maltosyl α-glucoside and α-maltosyl β-glucoside obtained by the method in Example A-5, 1 part by weight of α-glycosyl rutin and appropriate amounts of vitamin E and germicidal agent were dissolved in usual manner by heating, and the mixture was added with 5 parts by weight of 1,3-butylene glycol, 0.1 part by weight of carboxyvinyl polymer and 85.3 parts by weight of refined water and emulsified with homogenizer to obtain milky lotion.

The product is a moisture-retaining milky lotion which is favorably usable as sun screening agent and skin-whitening agent.

Example B-12

Skin Cream

Two parts by weight of polyoxyethylene glycol monostearate, 5 parts by weight of self-emulsifying glycerine monostearate, 2 parts by weight of α-glycosyl rutin, 1 part by weight of liquid paraffin, 10 parts by weight of glycerol trioctanate, 4 parts by weight of high-purity non-reducing oligosaccharide powder obtained by the method in Example A-7 and an appropriate amount of antiseptic were dissolved in usual manner by heating, and the resultant solution was added with 5 parts by weight of 1,3-butylene glycol and 66 parts by weight of refined water, emulsified with homogenizer and admixed with an appropriate amount of flavoring agent by stirring to obtain skin cream.

The product is a well-spreading cream which is favorably usable as sun screening cream, skin-refining agent and skin-whitening agent.

Example B-13

Dentifrice

Forty-five parts by weight of calcium hydrogen phosphate, 1.5 parts by weight of sodium laurate, 25 parts by weight of glycerine, 0.5 parts by weight of polyoxyethylene sorbitan laurate, 15 parts by weight of a syrup containing non-reducing oligosaccharides obtained by the method in Example A-3, 0.02 parts by weight of saccharin and 0.05 parts by weight of antiseptic were mixed with 13 parts by weight of water to obtain dentifrice.

The product, having a superior gloss and detergency, is suitable as dentifrice.

Example B-14

Intubation Feeding

A composition consisting of 20 parts by weight of a high-purity a-maltotriosyl β-glucoside powder obtained by the method in Example A-6, 1.1 parts by weight of glycine, 1 part by weight of sodium glutamate, 0.4 parts by weight of calcium lactate, 0.1 part by weight of magnesium carbonate, 0.01 part by weight of thiamine and 0.01 part by weight of riboflavin was divided into 24 g aliquot in small laminated aluminum packs which were then heat-sealed.

One pack of the product is dissolved in about 300–500 ml water and the resultant solution is usable as an a supplemental feeding parenterally administered to the nasal cavity, stomach or intestine.

The product is also favorably usable as intubation feeding for domestic animals through parenteral route and for human.

Example B-15

Intubation Feeding

A composition consisting of 580 parts by weight of a high-purity α-maltotriosyl β-glucoside powder obtained by the method in Example A-6, 190 parts by weight of dried york, 209 parts by weight of deferred milk, 4.4 parts by weight of sodium chloride, 1.85 parts by weight of potassium chloride, 4 parts by weight of magnesium sulfate, 0.01 part by weight of thiamine, 0.1 part by weight of sodium ascorbate, 0.6 parts by weight of vitamin E and 0.04 parts by weight of nicotine amide was divided into 25 g aliquot in small laminated aluminum packs which were then heat-sealed.

One pack of the product is dissolved in about 150–300ml water and the resultant solution is usable as an a supplemental feeding parenterally administered to the nasal cavity, stomach or intestine.

Example B-16

Liquid Interferon Agent

A natural human interferon-γ preparation, produced by Hayashibara Biochemical Laboratories, Inc., Okayama, Japan and commercialized by Cosmo Bio Co., Ltd., Tokyo, Japan, was subjected in usual manner to an immobilized anti-human interferon-γ antibody column to adsorb thereto the natural human interferon-γ in the preparation and to pass the calf serum albumin as stabilizer through the column for removal, and the adsorbed natural human interferon-γ was eluted by using a physiological saline which contained a high-purity β-maltosyl α-maltoside obtained by the method in Example A-5 in an amount of 7 w/w %, while changing the pH in the saline. Thereafter the eluate was subjected to membrane filtration and sterilely bottled in vials to obtain a liquid agent which contained $10^5$ units/ml of natural human interferon-γ.

The liquid agent is favorably usable in the treatment of vital diseases, allergic diseases, rheumatism, diabetes and malignant tumors where the liquid agent is perorally or parenterally administered at a dose of 1–20 ml/day/adult.

The liquid agent retains its initial activity even when allowed to stand at 4° C. or 25° C. for 20 days because β-maltosyl α-maltoside acts as stabilizer.

Example B-17

Liquid Tumor Necrosis Factor Agent

A natural human tumor necrosis factor-α preparation, produced by Hayashibara Biochemical Laboratories, Inc., Okayama, Japan and commercialized by Cosmo Bio Co., Ltd., Tokyo, Japan, was subjected in usual manner to an immobilized anti-human tumor necrosis factor-α antibody column to adsorb thereto the natural human tumor necrosis factor-α in the preparation and to pass the calf serum albumin as stabilizer through the column for removal, and the adsorbed natural human tumor necrosis factor-α was eluted by using a physiological saline containing a high-purity β-maltosyl α-maltoside obtained by the method in Example A-5 in an amount of 10 w/w %, while changing the pH in the saline. Thereafter the eluate was subjected to membrane filtration and sterilely bottled in vials to obtain a liquid agent which contained $10^4$ units/ml of natural human tumor necrosis factor-α.

The liquid agent is favorably usable in the treatment of vital diseases, allergic diseases, rheumatism, diabetes and malignant tumors where the liquid agent is perorally or parenterally administered at a dose of 1–20 ml/day/adult.

The liquid agent retains its initial activity even when allowed to stand at 4° C. or 25° C. for 20 days because β-maltosyl α-maltoside acts as stabilizer.

Example B-18

Interferon Tablet

A natural human interferon-α preparation, produced by Hayashibara Biochemical Laboratories, Inc., Okayama, Japan and commercialized by Cosmo Bio Co., Ltd., Tokyo, Japan, was subjected in usual manner to an immobilized anti-human interferon-α antibody column to adsorb thereto the natural human interferon-α in the preparation and to pass the calf serum albumin as stabilizer through the column for removal, and the adsorbed natural human interferon-α was eluted by using a physiological saline which contained a high-purity β-maltotriosyl α-glucoside obtained by the method in Example A-5 in an amount of 5 w/w %, while changing the pH in the saline. Thereafter the resultant eluate was subjected to membrane filtration, dehydrated and pulverized by the addition of about 20-fold amount of "Finerose T", a crystalline anhydrous maltose powder commercialized by Hayashibara Shoji Co., Ltd., Okayama, Japan and the resultant powder was fed to tabletting machine to obtain tablets (about 200 mg each) which contained about 150 units/tablet of natural human interferon-α.

The tablet is favorably usable as lozenge in the treatment of vital diseases, allergic diseases, rheumatism, diabetes and malignant tumors where the tablet is perorally administered at a dose of about 1–10 tablets/day/adult. In particular, the tablet is favorably usable as therapeutic agent for AIDS and hepatitis patients which have been rapidly increasing in recent years.

The tablet retains its initial activity over an extended time period even when allowed to stand at room temperature because β-maltotriosyl α-glucoside acts together with crystalline anhydrous maltose as stabilizer.

As evident from the above description, the non-reducing oligosaccharide of this invention is a non-reducing oligosaccharide with neotrehalose structure in the molecule, represented by the general formula of β-D-oligoglucosyl α-D-glucoside, α-D-oligoglucosyl β-D-glucoside or α-D-oligoglucosyl α-D-oligoglucoside, which is very stable and readily soluble in water, as well as having a superior quality and reduced sweetness. Further the non-reducing oligosaccharide of this invention has a chemical stability and properties of stabilizing amino acids and oligopeptides which readily cause browning reaction, as well as properties of stabilizing biologically-active substances whose activity or active ingredient readily inactivates. Still further the non-reducing oligosaccharide of this invention has additional features of controlling osmotic pressure, activating property, imparting gloss, retaining moisture, having an appropriate viscosity, preventing crystallization of other saccharides, having less fermentability and preventing retrogradation of amylaceous substances. These features are favorably utilizable in the production of various compositions including foods, beverages, cosmetics, pharmaceuticals. These would make a great contribution in the art.

Thus establishment of non-reducing oligosaccharide with neotrehalose structure represented by the general formula of β-D-oligoglucosyl α-D-glucoside, α-D-oligoglucosyl β-D-glucoside or β-D-oligoglucosyl α-D-oligoglucoside according to this invention and its production and use would have an industrial significance in the field of foods, beverages, cosmetics and pharmaceuticals.

While there has been described what is at present considered to be the preferred embodiments of the invention, it will ne understood the various modifications may be made therein, and it is intended to cover in the appended claims all such modifications as fall within the true spirits and scope of the invention.

We claim:

1. A composition in the form of a food or beverage, comprising an edible substance carrier and 0.5% w/w % or more, on a dry solid basis, of a non-reducing oligosaccharide of the formula:

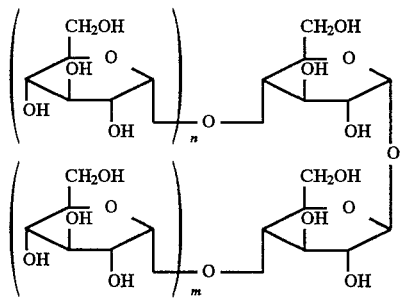

where "n" and "m" are 0 or more integers, and their total number (n+m) is at least 1.

2. The composition of claim 1, wherein said non-reducing oligosaccharide is one or more members selected from the group consisting of β-D-maltosyl α-D-glucoside, α-D-maltosyl β-D-glucoside, β-D-maltotriosyl α-D-Glucoside, α-D-maltotriosyl β-D-glucoside and β-D-maltosyl α-D-maltoside.

3. A pharmaceutical composition comprising a pharmaceutically active agent and a pharmaceutically acceptable carrier, further comprising 0.5% w/w % or more, on a dry solid basis, of a non-reducing oligosaccharide of the formula:

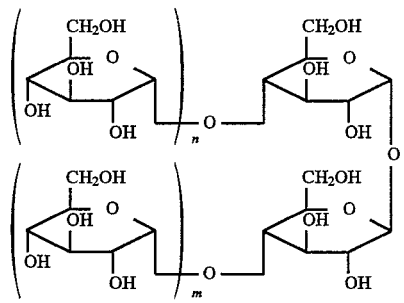

where "n" and "m" are 0 or more integers, and their total number (n+m) is at least 1.

4. A composition in the form of a food or beverage, a cosmetic or a pharmaceutical, which comprises a carrier and a non-reducing oligosaccharide, wherein said carrier is a food or beverage component, a cosmetic component or a pharmaceutical excipient, wherein said non-reducing oligosaccharide is present in an amount of 0.5 w/w % or more on a dry solid basis, and is of the formula:

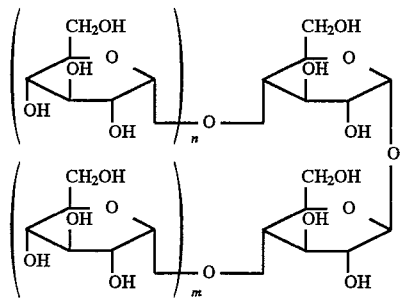

where "n" and "m" are 0 or more integers, and their total number (n+m) is at least 1.

5. The composition of claim 3, wherein said non-reducing oligosaccharide is one or more members selected from the group consisting of β-D-maltosyl α-D-glucoside, α-D-maltosyl β-D-glucoside, β-D-maltotriosyl α-D-glucoside, α-D-maltotriosyl β-D-glucoside and β-D-maltosyl α-D-maltoside.

6. The composition of claim 4, wherein said non-reducing oligosaccharide is one or more members selected from the group consisting of β-D-maltosyl α-D-glucoside, α-D-maltosyl β-D-glucoside, β-D-maltotriosyl α-D-glucoside, α-D-maltotriosyl β-D-glucoside and β-D-maltosyl α-D-maltoside.

* * * * *